United States Patent [19]
Dobak, III

[11] Patent Number: 5,275,595
[45] Date of Patent: Jan. 4, 1994

[54] CRYOSURGICAL INSTRUMENT

[76] Inventor: John D. Dobak, III, 6273 Caminito Del Oeste, San Diego, Calif. 92111

[21] Appl. No.: 908,416

[22] Filed: Jul. 6, 1992

[51] Int. Cl.$^5$ .............................. A61B 17/36
[52] U.S. Cl. ...................... 606/23; 606/24; 606/20
[58] Field of Search ............ 606/20, 21, 22, 23, 606/24, 25, 26

[56] References Cited

U.S. PATENT DOCUMENTS

| | | | |
|---|---|---|---|
| 3,439,680 | 4/1969 | Thomas, Jr. | 606/24 |
| 3,613,689 | 10/1971 | Trumbell et al. | 606/23 |
| 3,630,203 | 12/1971 | Sellinger et al. | 606/24 |
| 3,889,680 | 6/1975 | Armao | 606/23 |
| 3,971,383 | 7/1976 | van Gerven | 606/23 |
| 4,275,734 | 6/1981 | Mitchiner | 606/23 |
| 4,377,168 | 3/1983 | Rzasa et al. | 606/24 |
| 5,078,713 | 1/1992 | Varney | 606/23 |

Primary Examiner—Peter A. Aschenbrenner
Attorney, Agent, or Firm—Charles C. Logan, II

[57] ABSTRACT

A closed cycle cryosurgical instrument having a mixed gas assembly that is mounted in a housing and also having a cryosurgical probe unit. By using special (or certain) gas mixtures as opposed to pure gasses, pressure reductions to ≃ or ¼ of that required by pure gasses can be obtained. The use of gas mixtures with their attendant lower pressures allows for a closed cycle system since expensive and complex multi-stage compressors are not required. With the gas mixtures it is possible to obtain temperatures in the range of liquid nitrogen using a Joule-Thomson based system.

9 Claims, 1 Drawing Sheet

CRYOSURGICAL INSTRUMENT

BACKGROUND OF THE INVENTION

The present invention generally relates to apparatus including a cryosurgical probe of the type suitable for destroying diseased or degenerated cells in a living being by freezing such cells, and particularly to a surgical probe for administering a freezing treatment to abnormal cells in areas which may be embedded in or surrounded by healthy body tissue without injury to the healthy body tissue.

Since the introduction of the first cryoprobe by Dr. Cooper in 1964, cryosurgery, or the freezing of tissue for destruction, has steadily grown to become a concrete therapeutic modality in the medical, dental, and veterinary fields. In particular, cryosurgery gained wide acceptance in the gynecological and dermatological specialties. However, the technique has only enjoyed modest success in other areas of medicine, such as urology and neurosurgery. This is undoubtedly related to limitations of the early engineered devices which remain in use today with little modification. Growth of new cryosurgical technology and instrumentation was judged to be at a near standstill following the Eight Annual Meeting of the American College of Cryosurgery in 1988, and it was felt the future growth of cryosurgery depended on the development of high cooling capacity devices with increased precision and the flexibility to be used endoscopically and percutaneously. Current cryosurgical instrumentation employs liquid nitrogen or nitrous oxide as coolant materials, both of which contribute to the existing limitations. Liquid nitrogen is either sprayed onto tissue or circulated to a probe which is applied to tissue. The advantage of liquid nitrogen is its extremely low temperature ($-190°$ C.) which gives it a high cooling capacity. However, liquid nitrogen is evaporated during use, and thus requires continual replacement as well as storage vessels. Other disadvantages of liquid nitrogen systems include: relative complexity of probes which require high vacuum insulation and create problems with miniaturization for endoscopic use, cumbersome to use due to thick insulated hoses which circulate the coolant to the probe and which can become rigid during use, discomfort to the user due to cooling of the probe handle, and cooling of the entire shaft of the probe making the device less ideal for endoscopic procedures due to tissue freezing along the shaft's length.

Nitrous oxide (as a single gas) at high pressure is most commonly expanded through a Joule-Thomson valve in the end of a probe tip to cause cooling. The drop in pressure across the valve causes the cooling. Because the nitrous oxide is at room temperature until it reaches the probe tip, the insulation requirements of the liquid nitrogen system are not necessary, While this allows for easy miniaturization, greater precision and greater flexibility, cooling to only $-79°$ C. can be achieved, which is not suitable for cancerous or large lesions. Similar to liquid nitrogen, nitrous oxide is also lost during use, and the devices must be used in well ventilated areas due to nitrous oxide narcosis.

It is an object of the invention to provide a novel cryosurgical instrument that would combine the versatility of the nitrous oxide devices with the cooling capacity of liquid nitrogen devices.

It is also an object of the invention to provide a novel cryosurgical instrument wherein the system producing the cooling is preferably in a closed circuit so that the coolant materials can be recirculated, eliminating the need for replenishment.

It is another object of the invention to provide a novel cryosurgical instrument that would utilize a mixed-gas Joule-Thomson refrigeration technology (adiabatic expansion of multiple mixed gases across a valve).

It is an additional object of the invention to provide a novel high cooling capacity (near liquid N2 and much higher than nitrous oxide) Joule-Thomson device with the flexibility and versatility to be employed in endoscopic, percutaneous, and standard cryosurgical procedures.

It is a further object of the invention to provide a novel cryosurgical instrument that could be used in areas that have difficult access to liquid nitrogen.

SUMMARY OF THE INVENTION

The novel cryosurgical instrument has a mechanical compressor connected by flexible tubing to a cryosurgical probe. The compressor compresses a gas mixture such as ethane, nitrogen, and neon. These gases would then flow to the probe, and cause the tip to cool by passing through a Joule-Thomson valve. Other gas mixtures could also be used and the principle of using adiabatic expansion of mixed gases across a Joule-Thomson valve is being employed to create a cryosurgical instrument which can reach temperatures to near absolute zero. By using appropriate gas mixtures containing any fluid combination allowed from neon, nitrogen, various hydrocarbons, argon, oxygen, carbon monoxide, hydrogen sulfide, fluorocarbons, etc., an enhancement of the Joule-Thomson effect occurs, causing extreme temperature drops which cannot occur using single gases as in the nitrous oxide devices. Addition of fluorocarbons to the mixture helps prevent clogging of the Joule-Thomson valve. It may be that liquefaction of the gases would occur as they pass through the valve. In such a situation a slightly different design probe tip might be utilized. The Joule-Thomson valve in this probe design could be placed upstream from the tip and allow the liquified gases to flow freely to the tip and cool it as a phase change from liquid to gas occurs.

The gases pass back up the probe and are recirculated to the compressor to close the circuit. Because lower pressures are needed to produce cooling using mixed gas Joule-Thomson principles, it is possible to compress the gases returning from the probe. This is in contrast to nitrous oxide systems which require much higher pressures to produce even less cooling. Appropriate heat exchangers between the inflow of gas to the probe and outflow are constructed to minimize loss of cooling capacity and cooling of the tubing between the compressor and the probe. Changing the pressure and/or flow rate of the gas could allow for temperature variation at the tip. Miniature thermocouples could be placed in the tip to monitor the temperature. Additionally, a nerve stimulator could be placed in the tip for use in freezing nerves. A cutoff valve in the outflow tract of the probe, which, when activated would obstruct outflow, could cause the pressures across the Joule-Thomson valve to equilibrate, resulting in rapid warming of the tip, allowing for disengagement of the tip from tissue.

DESCRIPTION OF THE PREFERRED EMBODIMENT

The novel closed cycle cryosurgical instrument will now be described by referring to FIGS. 1-3 of the drawing. The cryosurgical instrument is generally designated numeral 10.

Cryosurgical instrument 10 has a mixed gas assembly 12 and a cryosurgical probe unit 14.

Figures 1, 2, 3:
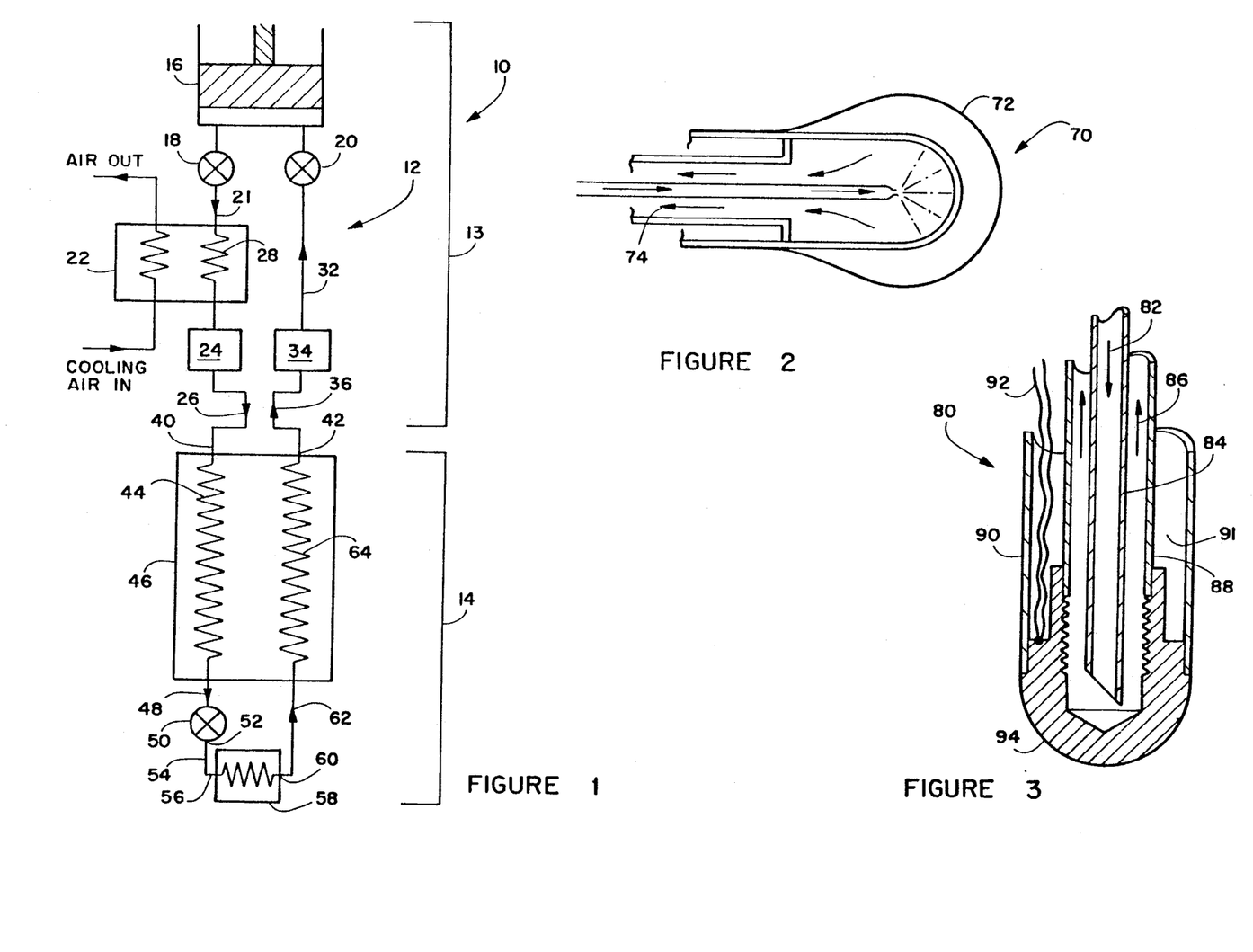
FIG. 1 is a schematic diagram of the novel cryosurgical instrument.
FIG. 2 is a partial cross sectional view of the probe tube tip with a Joule-Thomson valve.
FIG. 3 is an alternative embodiment of the probe tip when liquefaction of the gases occur.

Mixed gas assembly 12 is schematically illustrated in FIG. 1 contained in a housing 13. It has a gas compressor 16 having an outlet valve 18 and an inlet valve 20. Tubing 21 passes through ambient exchanger 22 and filter/dryer unit 24 on its way to hose connection 26. Filter/dryer unit 24 is provided to remove contaminants in the same manner as it does in a Freon refrigeration system. Ballast tank 34 serves a similar purpose to the receiver in a Freon refrigeration system. Ambient beat exchanger 22 could consist of a stainless steel tube coil 28 with air blowing over it to dissipate the heat of compression. Inlet valve 20 of gas compressor 16 is connected to tubing 32 that passes through ballast tank 30 34 on its way to hose connection 36.

Cryosurgical probe unit 14 has an inlet port 40 and an outlet port 42. Tubing 44 passes through counter-flow heat exchanger 46 and is connected to the inlet end 48 of a Joule-Thomson valve 50. Counter-flow heat exchanger 46 cools the gas supplied to the J-T valve so that the low temperatures required can be achieved. The high-pressure gas expands through the J-T valve and cooling occurs through the Joule-Thomson effect. The outlet end 52 of the J-T valve 50 is connected to tubing 54 that is connected to the inlet end 56 of cryosurgical probe tip 58. The heat sink is the tip of cryosurgical instrument probe tip 58 which absorbs heat while freezing the tissue and transfers it to the cold gas. The high pressure warm gas leaves the outlet end 60 of the cryosurgical probe tip 58 and is connected to the inlet end 62 of tubing 64 passing through the counter-flow heat exchanger 46. The high pressure warm gas is cooled in the counter-flow heat exchanger by heating the low pressure cold gas from the tip of the probe as it returns to the compressor inlet. Counter-flow heat exchanger 46 is part of the cryosurgical probe unit 14 and it consists of a tube coil 64 with high pressure gas flowing in the tube and low pressure gas flowing outside the tube in a counter current arrangement. Thermal insulation is provided around the counter-flow beat exchanger to prevent heat transfer from the ambient which would reduce performance.

One example of a probe tip 70 with a Joule-Thomson valve 72 is illustrated in FIG. 2. As the mixed gases expand through the J-T valve 72, they could potentially provide maximum cooling One example of a probe tip 90 with a Joule-Thomson valve 72 is illustrated in FIG. 2. As the mixed gases expand through the J-T valve 72, they could potentially provide maximum cooling in the range of $-180°$ C. The gases would return to compressor 16 through the outflow tube 74.

A liquefaction probe tip 80 is schematically illustrated in FIG. 3. This probe tip could be used should liquefaction of the gases occur. A Joule-Thomson valve would placed immediately upstream from the tip such as seen in FIG. 1. In this embodiment liquid gases 82 pass through feed line 84 and return as vapor 86 in exhaust line 88. An outer jacket 90 provides a vacuum chamber 91 and functions as insulation structure. A thermocouple 92 is attached to probe tip 94 to monitor the temperature of the tip.

Some examples of gas mixtures are set forth below along with the pressures required to achieve a particular temperature and the cooling capacity of the mixed gases at the temperature achieved. These samples list the gases in their proportions (mole fractions) as the number of moles for each gas:

| GAS MIXTURES | PRESSURES | TEMP | COOLING CAPACITY (WATTS) |
|---|---|---|---|
| 0.4C H + 0.4N + 0.2Ne | 44.1 psi | 65K | 1.0 |
| 0.6N + 0.3 CC1F (R13) + 0.1C H | 773 psi | 81.7K | 1.37 |
| 0.77N + 0.23(R14)CF | 1331 psi | 79K | .20 |
| 0.3N + 0.35CH + 0.35C H | 734 psi | 85K | 5.0 |

What is claimed is:

1. A cryosurgical instrument comprising:
   a mixed gas assembly having a compressor connected to an inlet valve and an outlet valve, a mixed gas mixture having a temperature colder than $-90$ degrees C. at a pressure less than 740 psi;
   a cryosurgical probe unit comprising an inlet port and an outlet port, a Joule-Thomson valve having an inlet end and an outlet end, a cryosurgical probe tip, a first connecting means for connecting said inlet port to said inlet end of said Joule-Thomson valve, a second connecting means for connecting the outlet end of said Joule-Thomson valve to the inlet end of salad cryosurgical probe tip, a third connecting means for connecting the outlet end of said cryosurgical probe tip to the outlet end of said cryosurgical probe unit;
   a fourth connecting means for connecting the outlet valve of said compressor to the inlet port of said cryosurgical probe unit; and
   a fifth connecting means for connecting the outlet port of said cryosurgical probe unit to the inlet valve of said gas compressor.

2. A cryosurgical instrument as recited in claim 1 wherein said first and third connecting means pass through a counter-flow beat exchanger.

3. A cryosurgical instrument as recited in claim 1 wherein said mixed gas assembly further comprises an ambient heat exchanger and said fourth connecting means passes therethrough to help remove heat from the mixed gas passing through said fourth connecting means.

4. A cryosurgical instrument as recited in claim 3 further comprising a filter/dryer unit in series after said ambient heat exchanger and said fourth connecting means passes therethrough.

5. A cryosurgical instrument as recited in claim 1 wherein said mixed gas assembly further comprises a ballast tank through which salad fifth connecting means passes.

6. A cryosurgical instrument as recited in claim 1 wherein said mixed gas assembly is mounted in a housing.

7. A cryosurgical instrument comprising:

a source of mixed gases in a housing having an inlet valve and an outlet valve, a mixed gas mixture having a temperature colder than −90 at degrees C. at a pressure less than 740 psi;

a cryosurgical probe unit comprising an inlet port and an outlet, means for allowing the mixed gases to expand across a primary structure having an inlet end and an outlet end, a cryosurgical probe tip, a first connecting means for connecting said inlet port to said inlet end of said primary structure, a second connecting means for connecting the outlet end of said primary structure to the inlet end of said cryosurgical probe tip, a third connecting means for connecting the outlet end of said cryosurgical probe tip to the outlet end of said cryosurgical probe unit;

a fourth connecting means for connecting the outlet valve of said compressor to the inlet port of said cryosurgical probe unit; and a fifth connecting means connected to the outlet port of said cryosurgical probe unit.

8. A cryosurgical instrument as recited in claim 7 further comprising cooling means for pre-cooling the gases exiting the outlet valve of the housing for the source of mixed gases.

9. A method comprising the step of using mixed gas a mixture having a temperature colder than −90 degrees C. at a pressure less than 740 psi cooling in a cryosurgical unit for medical purposes that require cold temperatures to alter tissue.

* * * * *

US005275595C1

(12) REEXAMINATION CERTIFICATE (4684th)
United States Patent
Dobak, III (10) Number: US 5,275,595 C1
(45) Certificate Issued: Dec. 17, 2002

(54) CRYOSURGICAL INSTRUMENT

(75) Inventor: John D. Dobak, III, San Diego, CA (US)

(73) Assignee: CryoGen, Inc., San Diego, CA (US)

Reexamination Request:
No. 90/005,696, Apr. 5, 2000
No. 90/005,900, Jan. 3, 2001

Reexamination Certificate for:
Patent No.: 5,275,595
Issued: Jan. 4, 1994
Appl. No.: 07/908,416
Filed: Jul. 6, 1992

(51) Int. Cl.⁷ .............................................. A61B 18/18
(52) U.S. Cl. ............................ 606/23; 606/24; 606/20
(58) Field of Search .................................. 606/20–26

(56) References Cited

U.S. PATENT DOCUMENTS

| | | |
|---|---|---|
| 2,319,542 A | 5/1943 | Hall |
| 2,672,032 A | 3/1954 | Towse |
| 3,439,680 A | 4/1969 | Thomas, Jr. |
| 3,613,689 A | 10/1971 | Trumbell et al. |
| 3,630,203 A | 12/1971 | Sellinger et al. |
| 3,729,945 A | 5/1973 | Linnet |
| 3,750,417 A | 8/1973 | Johannes et al. |
| 3,827,436 A | 8/1974 | Stumpf et al. |
| 3,889,680 A | 6/1975 | Armao |
| 3,913,581 A | * 10/1975 | Ritson et al. .................. 606/23 |
| 3,924,628 A | 12/1975 | Droegemueller et al. |
| 3,932,154 A | 1/1976 | Coers et al. |
| 3,971,383 A | 7/1976 | van Gerven |
| 4,201,319 A | 5/1980 | Andera et al. |
| 4,206,609 A | 6/1980 | Durenec |
| 4,275,734 A | 6/1981 | Mitchiner |
| 4,377,168 A | 3/1983 | Rzasa et al. |
| 4,601,296 A | 7/1986 | Yerushalmi |
| 5,063,747 A | 11/1991 | Jones |
| 5,522,870 A | 6/1996 | Ben-Zion |

FOREIGN PATENT DOCUMENTS

| | | |
|---|---|---|
| EP | 0271989 | 6/1998 |
| FR | 1465540 | 1/1967 |
| FR | 1468862 | 2/1967 |
| FR | 2 482 445 | 3/1980 |
| GB | 1336892 | 11/1973 |

(List continued on next page.)

OTHER PUBLICATIONS

E. Bodio, "The Application of Multiple–Component Gaseous Mixtures in Linde–Hampson Type Refrigerators" Proceedings of the Institute of Thermal Technology and Fluid Mechanics, Wroclaw Polytechnic Institute, (Wroclaw Polytechnic Institure, 1985) (Polish version and translation supplied).

A.P. Grokholskii et al., "*The Krioelektronika–1' Cryogenic Dental Unit*," 3 Medicinskaya Tekhnika [Medical Technology] at 16–20 (1982) (Russian version and translation supplied).

Kobrianski et al., "*A Cryomedical Device Based on a Closed Cycle Joule–Thomson Cooling System*" Nos. 8–9 Elektronnaya Promyschlennost [Electronics Industry] at 71–72 (1979) (Russian version and translation supplied).

JPL Technology Utilization Office, Technical Support Package on Mixed–Gas Sorption Joule–Thomson Refrigerator (Jet Propulsion Laboratory, Pasadena, CA, May 1991).

(List continued on next page.)

*Primary Examiner*—Michael Peffley (57) ABSTRACT

A closed cycle cryosurgical instrument having a mixed gas assembly that is mounted in a housing and also having a cryosurgical probe unit. By using special (or certain) gas mixtures as opposed to pure gasses, pressure reductions to [≈] ⅓ or ¼ of that required by pure gasses can be obtained. The use of gas mixtures with their attendant lower pressures allows for a closed cycle system since expensive and complex multi-stage compressors are not required. With the gas mixtures it is possible to obtain temperatures in the range of liquid nitrogen using a Joule-Thomson based system.

FOREIGN PATENT DOCUMENTS

| | | |
|---|---|---|
| GB | 2 026 324 | 2/1980 |
| GB | 2 093 964 | 9/1982 |
| GB | 2 283 678 | 5/1995 |
| GB | 2289412 | 11/1995 |
| GB | 2 289 413 | 11/1995 |
| GB | 2 289 414 | 11/1995 |
| GB | 2 289 510 | 11/1995 |
| JP | 57-126430 | 8/1982 |
| SU | 333857 | 4/1974 |
| SU | 333858 | 4/1974 |
| SU | 527467 | 9/1976 |
| SU | 534484 | 11/1976 |
| SU | 565052 | 7/1977 |
| SU | 573496 | 9/1977 |
| SU | 627154 | 10/1978 |
| SU | 637417 | 12/1978 |
| SU | 676604 | 7/1979 |
| SU | 907054 | 7/1980 |
| SU | 768795 | 10/1980 |
| SU | 802348 | 2/1981 |
| SU | 802349 | 2/1981 |
| SU | 802350 | 2/1981 |
| SU | 802351 | 2/1981 |
| SU | 832268 | 5/1981 |
| SU | 918298 | 4/1982 |
| SU | 966107 | 10/1982 |
| SU | 986107 | 10/1982 |
| SU | 1026795 | 7/1983 |
| SU | 1026796 | 7/1983 |
| SU | 1054400 | 11/1983 |
| SU | 1089099 | 4/1984 |
| SU | 1090699 | 5/1984 |
| SU | 1134856 | 1/1985 |
| SU | 1158567 | 5/1985 |
| SU | 1189434 | 11/1985 |
| SU | 1437012 | 11/1986 |
| WO | WO 93/04647 | 3/1993 |
| WO | WO 93/08753 | 5/1993 |
| WO | WO 95/30379 | 11/1995 |
| WO | WO 95/30380 | 11/1995 |

OTHER PUBLICATIONS

W.A. Little, "*Advances in Joule–Thomson Cooling*" 35 Advances in Cryogenic Engineering 1305–1314 (1990) ("Little I").

W.A. Little, "*Microminiature Refrigeration*," 55 (5) Rev. Sci. Instrum. at 661–680 (May 1984 ("Little II").

CryoGen's Initial Brief in Support its Construction of Claims 1–9 of U.S. Pat. No. 5,275,595 for "Cryosurgical Instrument", *FemRx, Inc. V. CryoGen, Inc.,* Case No. C98–02330 VRW (N.D. Cal. filed Jun. 8, 1998); *CryoGen, Inc. v. Johnson & Johnson, Inc.,* Case No. C99–02471 VRW (N.D. Cal. filed May 25, 1999) (consolidated).

Declaration of Nicolas S. Gikkas in Support of CryoGen's Brief in Supporting Its Construction of Claims 1–9 of U.S. Pat. No. 5,275,595 for "Cryosurgical Instrument", *FemRx, Inc. V. CryoGen, Inc.,* Case No. C98–02330 VWR (N.D. Cal. filed Jun. 8, 1998); *CryoGen, Inc. V. Johnson & Johnson, Inc.,* Case No. C99–02471 VRW (N.D. Cal. filed May 25, 1999) (consolidated).

Ethicon, Inc.'s Claim Construction Brief for U.S. Pat. No. 5,275,595, *FemRx, Inc. V. CryoGen, Inc.,* Case No. C98–02330 VRW (N.D. Cal. filed Jun. 8, 1998); *CryoGen, Inc. V. Johnson & Johnson, Inc.,* Case No. C99–02471 VRW (N.D. Cal. filed May 25, 1999) (consolidated).

Declaration of John A. Barclay, Ph.D. in Support of Ethicon's Claim Construction Brief Regarding U.S. Pat. No. 5,275,595, *FemRx, Inc. V. CryoGen, Inc.,* Case No. C98–02330 VRW (N.D. Cal. filed Jun. 8, 1998); *CryoGen, Inc. V. Johnson & Johnson, Inc.,* Case No. C99–02471 VRW (N.D. Cal. filed May 25, 1999) (consolidated).

Declaration of Ernest G. Cravalho, Ph.D. in Support of Ethicon's Claim Construction Brief Regarding U.S. Pat. No. 5,275,595, *FemRx, Inc. V. CryoGen, Inc.,* Case No. C98–02330 VRW (N.D. Cal. filed Jun. 8, 1998); *CryoGen, Inc. V. Johnson & Johnson, Inc.,* Case No. C99–02471 VRW (N.D. Cal. filed May 25, 1999) (consolidated).

Declaration of Peter J. Curtin in Support of Ethicon, Inc's Claim Construction Brief for U.S. Pat. No. 5,275,595, *FemRx, Inc. V. CryoGen, Inc.,* Case No. C98–02330 VRW (N.D. Cal. filed Jun. 8, 1998); *CryoGen, Inc. V. Johnson & Johnson, Inc.,* Case No. C99–02471 VRW (N.D. Cal. filed May 25, 1999) (consolidated).

CryoGen's Reply Brief in Support of the Construction of Claims 1–9 of U.S. Pat. No. 5,275,595, *FemRx, Inc. V. CryoGen, Inc.,* Case No. C98–02330 VRW (N.D. Cal. filed Jun. 8, 1998); *CryoGen, Inc. V. Johnson & Johnson, Inc.,* Case No. C99–02471 VRW (N.D. Cal. filed May 25, 1999) (consolidated).

Duane Everett Townsend, M.D. F.A.C.O.G.'s Declaration in Support of CryoGen's Construction of Claims 1–9 of U.S. Pat. No. 5,275,595 for "Cryosurgical Instrument", *FemRx, Inc. V. CryoGen, Inc.,* Case No. C98–02330 VRW (N.D. Cal. filed Jun. 8, 1998); *CryoGen, Inc. V. Johnson & Johnson, Inc.,* Case No. C99–02471 VRW (N.D. Cal. filed May 25, 1999) (consolidated).

Dr. Graham Walker's Declaration in Support of CryoGen's Construction of U.S. Pat. No. 5,275,595 for "Cryosurgical Instrument", *FemRx, Inc. V. CryoGen, Inc.,* Case No. C98–02330 VRW (N.D. Cal. filed Jun. 8, 1998); *CryoGen, Inc. V. Johnson & Johnson, Inc.,* Case No. C99–02471 VRW (N.D. Cal. filed May 25, 1999) (consolidated).

Amoils, S.P., *The Joule Thomas Cryoprobe*, 78 Arch Opthal, Johaannesburg, South Africa, Aug., 1967.

Bodio, E., *Application of Multicomponent Gaseous Mixtures in Linde–Hampson Coolers*, Wroclaw Inst. of Tech. (1985) (with translation).

Brodjanskij, V.M., *Development of Low–Temperature Engineering Until 2000*, OEDB, 90:048732, 25:4 Luft–und Kaeltetechnik (German Democratic Republic) 193–195 (1989) (with translation).

Cryogen Documents, Bates Nos. CRY 000428—CRY 000479, Fig. at CRY 000468.

Gassanov, L.G. et al., *Experience in the Development and Operation of a Cryosurgical Apparatus*, Electronnaya Promyslennost 41–42 (No. 1, Jan.–Feb. 1987) (with translation).

Grokholsky, A.P. et al., *Cryogenic Dental System "Cryoelektronica–1"* Medicinskaya Tekhnika 16–20 (No. 3, May–Jun. 1982) (with translation).

Kleemenko, A.P., *One Flow Cascade Cycle* (*in Schemes of Natural Gas Liquefaction and Separation*), 1 International Congress of Refrigeration, Copenhagen 34–39 (1959).

Kobrianski, V.L. et al., *A Cryomedical Device Based on a Closed Cycle Joule–Thomson Cooling System*, Elektronnaya Promyshlennost (Electronics Industry), Nos. 8–9 at 71–72 (1979) (with translation).

Little, W.A., Handwriten Notes to Valley Laboratories, Bates Nos. M00001–M00009 (Apr. 1987).

Little, W.A., *Microminature Refrigerators for Joule–Thompson Cooling of Electronic Chips and Devices*, 35 Advances in Cryogenic Engineering 1325–1333 (1990).

Little, W.A., *Microminiature Refrigeration*, 55(5) Rev. Sci. Instrum. 661–680 (May 1984).

Little, W.A., *Recent Developments in Joule–Thompson Cooling Gases, Coolers and Compressors*, International Cryocoolers Conference (1988).

Little, W.A., *Advances in Joule–Thomson Cooling*, 35 Advances in Cryogenic Engineering 1305–1314 (1990).

Sood, S.K., *Prediction Methods for Vapour–Liquid Equilibrium in Multi–Component Cryogenic Mixtures*, Cryogenics 199–207 (Jun. 1970).

Torre, D., *Alternate Cryogens for Cryosurgery*, 1:2, Journal of Dermatological Surgery 56–58 (Jun. 1975).

CryoGen, Inc.'s Answer to Complaint and Countercam for Patent Infringement, *FemRx V. CryoGen, Inc.*, Case No. C98–02330 VRW (N.D. Cal.).

Plaintiff FemRx's Answer and Defenses to CryoGen's Counterclaim, *FemRx V. CryoGen, Inc.*, Case No. C98–02330 VRW (N.D. Cal.).

Answer and Counterclaims of Third–Party Defendant and Counterclaimant MMR Technologies, Inc., *FemRx V. CryoGen, Inc.*, Case No. C98–02330 VRW (N.D. Cal.).

First Amended Complaint, *FemRx V. CryoGen, Inc.*, Case No. C98–02330 VRW (N.D. Cal.).

FemRx, Inc.'s Amended Answer and Defenses to CryoGen's Counterclaim for Infringement of U.S. Pat. No. 5,275,595, *FemRx V. CryoGen, Inc.*, Case No. C98–02330 VRW (N.D. Cal.).

Jones, Jack A., *Cryogenic Mixed Fluid Application Study and Computer Code Development*, Final Report, Jet Propoulsion Laboratory (Jun. 1989–Dec. 1991).

Jones et al., *Mixed–Gas Sorption Joule–Thompson Refrigerator*, 15:5 NASA Tech Briefs 39–40 (May 1991).

Jones, J., Sorption Refrigeration Research at JPL/NASA, Sci. Tech. Froid 143–152 (International Institute of Refrigeration, Paris, France 1992).

Docket Street, *CryoGen, Inc. v. Johnson & Johnson, Inc.*, Case No. C99–02471 JL (N.D. Cal. filed May 25, 1999) (updated Mar. 30, 2000).

Docket Sheet, *FemRx, Inc. v. CryoGen, Inc.*, Case No. C98–02330 VRW (N.D. Cal. filed Jun. 8, 1998) (updated Mar 30, 2000).

* cited by examiner

/ US 5,275,595 C1

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, lines 32–58:

Cryosurgical probe unit 14 has an inlet port 40 and an outlet port 42. Tubing 44 passes through counter-flow heat exchanger 46 and is connected to the inlet end 48 of a Joule-Thomson valve 50. Counter-flow heat exchanger 46 cools the gas supplied to the J-T valve so that the low temperatures required can be achieved. The high-pressure gas expands through the J-T valve and cooling occurs through the Joule-Thomson effect. The outlet end 52 of the J-T valve 50 is connected to tubing 54 that is connected to the inlet end 56 of cryosurgical probe tip 58. The heat sink is the tip of cryosurgical instrument probe tip 58 which absorbs heat while freezing the tissue and transfers it to the cold gas. The [high] *low* pressure [warm] *cold* gas leaves the outlet end 60 of the cryosurgical probe tip 58 and is connected to the inlet end 62 of tubing 64 passing through the counter-flow heat exchanger 46. The high pressure warm gas is cooled in the counter-flow heat exchanger by heating the low pressure cold gas from the tip of the probe as it returns to the compressor inlet. Counter-flow heat exchanger 46 is part of the cryosurgical probe unit 14 and it consists of a tube coil 64 with high pressure gas flowing in the tube and low pressure gas flowing outside the tube in a counter current arrangement. Thermal insulation is provided around the counter-flow beat exchanger to prevent heat transfer from the ambient which would reduce performance.

Column 3, lines 59–68:

One example of a probe tip 70 with a Joule-Thomson valve 72 is illustrated in FIG. 2. [As the mixed gases expand through the J-T valve 72, they could potentially provide maximum cooling]

[One example of a probe tip 90 with a Joule-Thomson valve 72 is illustrated in FIG. 2.] As the mixed gases expand through the J-T valve 72, they could potentially provide maximum cooling in the range of –180° C. The gases would return to compressor 16 through the outflow tube 74.

AS A RESULT OF REEXAMINATION, IT HAS BEEN DETERMINED THAT:

Claims 8 and 9 are cancelled.

Claims 1–3, 5 and 7 are determined to be patentable as amended.

Claims 4 and 6, dependent on an amended claim, are determined to be patentable.

New claims 10–49 are added and determined to be patentable.

1. A cryosurgical instrument comprising:
   a mixed gas assembly having a compressor connected to an inlet valve and an outlet valve, a mixed gas mixture having a temperature colder then –90 degrees C. at a pressure less than 740 psi;
   a cryosurgical probe unit comprising an inlet port and an outlet port, a Joule-Thomson valve having an inlet end and an outlet end, a cryosurgical probe tip, a first connecting means for connecting said inlet port to said inlet end of said Joule-Thomson valve, a second connecting means for connecting the outlet end of said Joule-Thomson valve to the inlet end of [salad] *said* cryosurgical probe tip, a third connecting means for connecting the outlet end of said cryosurgical probe tip to the outlet end of said cryosurgical probe unit;
   a fourth connecting means for connecting the outlet valve of said compressor to the inlet port of said cryosurgical probe unit;
   *an ambient heat exchanger, said fourth connecting means passing there through to help remove heat from the mixed gas passing through said fourth connecting means;* and
   a fifth connecting means for connecting the outlet port of said cryosurgical probe unit to the inlet valve of said gas compressor.

2. A cryosurgical instrument as recited in claim 1 wherein said first and third connecting means pass through a counter-flow [beat] *heat* exchanger.

3. A cryosurgical instrument as recited in claim 1 wherein said [mixed gas assembly further comprises an] ambient heat exchanger [and said fourth connecting means passes therethrough to help remove heat from the mixed gas passing through said fourth connecting means] *comprises a stainless steel tube coil with air blowing over it to dissipate the heat of compression.*

5. A cryosurgical instrument as recited in claim 1 wherein said mixed gas assembly further comprises a ballast tank through which [salad] *said* fifth connecting means passes.

7. A cryosurgical instrument comprising:
   a source of mixed gases in a housing having an inlet valve and an outlet valve, a mixed gas mixture having a temperature colder than –90 at degrees C. at a pressure less than 740 psi;
   a cryosurgical probe unit comprising an inlet port and an outlet, means for allowing the mixed gases to expand across a primary structure having an inlet end and an outlet end, a cryosurgical probe tip, a first connecting means for connecting said inlet port to said inlet end of said primary structure, a second connecting means for connecting the outlet end of said primary structure to the inlet end of said cryosurgical probe tip, a third connecting means for connecting the outlet end of said cryosurgical probe tip to the outlet end of said cryosurgical probe unit;
   a fourth connecting means for connecting the outlet valve of said compressor to the inlet port of said cryosurgical probe unit; [and]
   a fifth connecting means connected to the outlet port of said cryosurgical probe unit; *and cooling means for* pre-cooling the gases exiting the outlet valve of the housing for the source of mixed gases, wherein said cooling means for pre-cooling the gases exiting the outlet valve of the housing for the source of mixed gases comprises an ambient heat exchanger having a stainless steel tube coil with air blowing over it to dissipate the heat of compression.

10. A cryosurgical instrument comprising:
a. a mixed gas assembly including a compressor having an inlet valve and an outlet valve, providing, at said outlet valve, a mixed gas mixture at a pressure of less than 740 psi;
b. a cryosurgical probe unit comprising:
   i. an inlet port and
   ii. an outlet port,
   iii. a Joule-Thomson valve having an inlet end and an outlet end,
   iv. a cryosurgical probe tip having an inlet and an outlet,
   v. a first connecting means for connecting said inlet port to said inlet end of said Joule-Thomson valve,
   vi. a second connecting means for connecting the outlet end of said Joule-Thomson valve to the inlet of said cryosurgical probe tip, and
   vii. a third connecting means for connecting the outlet of said cryosurgical probe tip to the outlet port of said cryosurgical probe unit;
c a fourth connecting means for connecting said outlet valve to the inlet port of said cryosurgical probe unit; and
d. a fifth connecting means for connecting said outlet port of said cryosurgical probe unit to said inlet valve;
e. said mixed gas mixture circulating from said compressor through said outlet valve, fourth connecting means, inlet port, first connecting means, Joule-Thomson valve, second connecting means, cryosurgical probe tip, third connecting means, outlet port, fifth connecting means and inlet valve, back to said compressor;
f. an ambient heat exchanger, said fourth connecting means passing there through to help remove heat from the mixed gas mixture passing through said fourth connecting means; and
g. said mixed gas mixture selected such that, after expanding through said Joule-Thomson valve at said pressure of less than 740 psi, it will have a temperature colder than −90 degrees C.

11. A cryosurgical instrument as recited in claim 10 wherein said pressure is equal to or less than 734 psi.

12. A cryosurgical instrument as recited in claim 10 and further including a counter-flow heat exchanger, said first and third connecting means passing through said counter-flow heat exchanger.

13. A cryosurgical instrument as recited in claim 10 wherein said counter-flow heat exchanger is disposed in said probe unit.

14. A cryosurgical instrument as recited in claim 13 wherein said counter-flow heat exchanger is insulated from the ambient.

15. A cryosurgical instrument as recited in claim 10 and further including a thermocouple in said probe tip.

16. A cryosurgical instrument as recited in claim 13 wherein said ambient heat exchanger comprises an ambient heat exchanger having a stainless steel tube coil with air blowing over it to dissipate the heat of compression.

17. A cryosurgical instrument as recited in claim 16 wherein said mixed gas assembly including said ambient heat exchanger is enclosed in a housing.

18. A cryosurgical instrument as recited in claim 10 and further comprising a filter/dryer unit in series after said ambient heat exchanger and said fourth connecting means passes therethrough.

19. A cryosurgical instrument as recited in claim 10 wherein said mixed gas assembly further comprises a ballast tank through which said fifth connecting means passes.

20. A cryosurgical instrument as recited in claim 19 wherein said mixture includes ethane, nitrogen and neon.

21. A method of altering tissue for medical purposes utilizing cold temperatures comprising the steps of:
a) generating a compressed mixture of gases at a pressure of less than 740 psi; and
b) passing the pressurized mixture through a Joule-Thomson valve in a cryosurgical unit having a probe tip to provide Joule-Thomson expansion to the mixture of gases, said mixture selected such that said expansion results in the temperature of said mixture being reduced to a temperature below −90 degrees C. whereby the temperature of said probe tip will be reduced;
c) recompressing the expanded mixture of gases for subsequent expansion reuse;
d) pre-cooling said compressed mixture of gases prior to expansion using the expanded mixture of gases prior to recompression;
e) further pre-cooling said compressed mixture of gases prior to said pre-cooling using ambient air; and
f) applying said probe tip to tissue to be altered.

22. A cryosurgical instrument as recited in claim 21 wherein said pressure is equal to or less than 734 psi.

23. A method accoridng to claim 21 and further comprising storing said mixture of gases in a ballast tank prior to recompression.

24. A method according to claim 21 and wherein said further pre-cooling of said compressed mixture of gases prior to said pre-cooling using ambient air is done by passing air over stainless steel tubing.

25. A method according to claim 24 and further comprising passing said compressed mixture of gases through filter/dryer unit after cooling with ambient air.

26. A method according to claim 25 wherein said mixture includes ethane, nitrogen and neon.

27. A method according to claim 21 wherein said medical purposes is a gyneoological purpose.

28. A method according to claim 21 wherein said tissue is internal to a patient's body.

29. A method according to claim 21 and further including re-warming said probe tip after cooling said probe to alter tissue.

30. A method according to claim 29 wherein said probe freezes tissue before said re-warming.

31. A method according to claim 21 wherein said gas mixture is selected to reduce clogging.

32. A method for performing cryosurgury to alter tissue for a medical purposes comprising:
providing a mechanical compressor connected by flexible tubing to a cryosurgical probe, the cryosurgical probe including a high pressure fluid path, a Joule-Thomson valve, and a low pressure fluid path, with the compressor, the high pressure fluid path, the Joule-Thomson valve, and the low pressure fluid path connected in a closed circuit;
compressing a gas mixture including at least a hydrocarbon with the compressor to a pressure of less than 740 psi;
precooling the compressed mixture in a two stage precooling wherein a first stage of precooling is carried out using ambient air to cool fluid in said high pressure path and a second stage is carried out using fluid in said low pressure path to cool fluid in said high pressure path in a countercurrent heat exchanger;
delivering the compressed mixture to the Joule-Thomson valve via the flexible tubing and the high pressure fluid path;
expanding the mixture through the Joule-Thomson valve to a temperature below −90 degrees C. so as to cool the probe to alter tissue for a medical purpose;
returning the expanded gas to the compressor through the flexible tubing and the low pressure path;
recompressing and recirculating the gas mixture in a closed circuit fashion.

33. A method of performing cryosurgury to alter tissue for a medical purposes comprising:
providing a mechanical compressor connected by flexible tubing to a cryosurgical probe, the cryosurgical probe including a high pressure fluid path, a Joule-Thomson valve, and a low pressure fluid path, with the compressor, the high pressure fluid path, the Joule-Thomson valve, and the low pressure fluid path connected in a closed circuit
compressing a gas mixture including at least argon with the compressor to a pressure of less than 740 psi;
precooling the compressed mixture in a two stage precooling wherein a first stage of precooling is carried out using ambient air to cool fluid in said high pressure path and a second stage is carried out using fluid in said low pressure path to cool fluid in said high pressure path in a countercurrent heat exchanger;
delivering the compressed mixture to the Joule-Thomson valve via the flexible tubing and the high pressure fluid path;
expanding the mixture through the Joule-Thomson valve to a temperature below −90 degrees C. so as to cool the probe to alter tissue for a medical purpose;
returning the expanded gas to the compressor through the flexible tubing and the low pressure path;
recompressing and recirculating the gas mixture in a closed circuit fashion.

34. A method of performing cryosurgury to alter tissue for a medical purposes comprising:
providing a mechanical compressor connected by flexible tubing to a cryosurgical probe, the cryosurgical probe including a high pressure fluid path, a Joule-Thomson valve, and a low pressure fluid path, with the compressor, the high pressure fluid path, the Joule-Thomson valve, and the low pressure fluid path connected in a closed circuit
compressing a gas mixture including at least oxygen with the compressor to a pressure of less than 740 psi;
precooling the compressed mixture in a two stage precooling wherein a first stage of precooling is carried out using ambient air to cool fluid in said high pressure path and a second stage is carried out using fluid in said low pressure path to cool fluid in said high pressure path in a countercurrent heat exchanger;
delivering the compressed mixture to the Joule-Thomson valve via the flexible tubing and the high pressure fluid path:
expanding the mixture through the Joule-Thomson valve to a temperature below −90 degrees C. so as to cool the probe to alter tissue for a medical purpose;
returning the expanded gas to the compressor through the flexible tubing and the low pressure path;
recompressing and recirculating the gas mixture in a closed circuit fashion.

35. A method of performing cryosurgury to alter tissue for a medical purposes comprising:
providing a mechanical compressor connected by flexible tubing to a cryosurgical probe, the cryosurgical probe including a high pressure fluid path, a Joule-Thomson valve, and a low pressure fluid path, with the compressor, the high pressure fluid path, the Joule-Thomson valve, and the low pressure fluid path connected in a closed circuit
compressing a gas mixture including at least carbon dioxide with the compressor to a pressure of less than 740 psi;
precooling the compressed mixture in a two stage precooling wherein a first stage of precooling is carried out using ambient air to cool fluid in said high pressure path and a second stage is carried out using fluid in said low pressure path to cool fluid in said high pressure path in a countercurrent heat exchanger;
delivering the compressed mixture to the Joule-Thomson valve via the flexible tubing and the high pressure fluid path;
expanding the mixture through the Joule-Thomson valve to a temperature below −90 degrees C. so as to cool the probe to alter tissue for a medical purpose;
returning the expanded gas to the compressor through the flexible tubing and the low pressure path;
recompressing and recirculating the gas mixture in a closed circuit fashion.

36. A method of performing cryosurgury to alter tissue for a medical purposes comprising;
providing a mechanical compressor connected by flexible tubing to a cryosurgical probe, the cryosurgical probe including a high pressure fluid path, a Joule-Thomson valve, and a low pressure fluid path, with the compressor, the high pressure fluid path, the Joule-Thomson valve, and the low pressure fluid path connected in a closed circuit compressing a gas mixture including at least hydrogen sulfide with the compressor to a pressure of less than 740 psi;

precooling the compressed mixture in a two stage precooling wherein a first stage of precooling is carried out using ambient air to cool fluid in said high pressure path and a second stage is carried our using fluid in said low pressure path to cool fluid in said high pressure path in a countercurrent heat exchanger;

delivering the compressed mixture to the Joule-Thomson valve via the flexible tubing and the high prsssure fluid path;

expanding the mixture through the Joule-Thomson valve to a temperature below −90 degrees C. so as to cool the probe to alter tissue for a medical purpose;

returning the expanded gas to the compressor through the flexible tubing and the low pressure path;

recompressing and recirculating the gas mixture in a closed circuit fashion.

37. A method of performing cryosurgury to alter tissue for a medical purposes comprising:

providing a mechanical compressor connected by flexible tubing to a cryosurgical probe, the cryosurgical probe including a high pressure fluid path, a Joule-Thomson valve, and a low pressure fluid path, with the compressor, the high pressure fluid path, the Joule-Thomson valve, and the low pressure fluid path connected in a closed circuit compressing a gas mixture including at least a flurocarbon with the compressor to a pressure of less than 740 psi;

precooling the compressed mixture in a two stage precooling wherein a first stage of precooling is carried out using ambient air to cool fluid in said high pressure path and a second stage is carried out using fluid in said low pressure path to cool fluid in said high pressure path in a countercurrent heat exchanger;

delivering the compressed mixture to the Joule-Thomson valve via the flexible tubing and the high pressure fluid path;

expanding the mixture through the Joule-Thomson valve to a temperature below −90 degrees C. so as to cool the probe to alter tissue for a medical purpose;

returning the expanded gas to the compressor through the flexible tubing and the low pressure path;

recompressing and recirculating the gas mixture in a closed circuit fashion.

38. A cryosurgical instrument as recited in claim 10 and further including means to warm said probe tip.

39. A cryosurgical instrument as recited in claim 38 wherein said means to warm said probe tip comprise a cutoff valve in the outflow tract of the probe, which, when activated acts obstruct outflow and cause the pressures across the Joule-Thomson valve to equilibrate, resulting in rapid warming of the tip, allowing for disengagement of the tip from tissue.

40. A cryosurgical instrument comprising:
a. a mixed gas assembly including a compressor having an inlet valve and an outlet valve, providing, at said outlet valve, a mixed gas mixture at a pressure of less than 740 psi:
b. a cryosurgical probe unit comprising:
  i. an inlet port and
  ii. an outlet port,
  iii. a Joule-Thomson valve having an inlet end and an outlet end,
  iv. a cryosurgical probe tip having an inlet and an outlet,
  v. a first connecting means for connecting said inlet port to said inlet end of said Joule-Thomson valve,
  vi. a second connecting means for connecting the outlet end of said Joule-Thomson valve to the inlet of said cryosurgical probe tip, and
  vii. a third connecting means for connecting the outlet of said cryosurgical probe tip to the outlet port of said cryosurgical probe unit;
c. a fourth connecting means for connecting said outlet valve to the inlet port of said cryosurgical probe unit; and
d. a fifth connecting means for connecting said outlet port of said cryosurgical probe unit to said inlet valve;
e. said mixed gas mixture circulating from said compressor through said outlet valve, fourth connecting means, inlet port, first connecting means, Joule-Thomson valve, second connecting means, cryosurgical probe tip, third connecting means, outlet port, fifth connecting means and inlet valve, back to said compressor;
f. a cutoff valve in the outflow tract of the probe, which, when activated acts to obstruct outflow and cause the pressures across the Joule-Thomson valve to equilibrate, resulting in rapid warming of the tip, allowing for disengagement of the tip from tissue; and
g. said mixed gas mixture selected such that, after expanding through said Joule-Thomson valve at said pressure of less than 740 psi, it will have a temperature colder than −90 degrees C.

41. A cryosurgical instrument as recited in claim 1 and further including a cutoff valve in the outflow tract of the probe, which, when activated acts obstruct outflow and cause the pressures across the Joule-Thomson valve to equilibrate, resulting in rapid warming of the tip, allowing for disengagement of the tip from tissue.

42. A cryosurgical instrument as recited in claim 7 and further including a cutoff valve in the outflow tract of the probe, which, when activated acts obstruct outflow and cause the pressures across the Joule-Thomson valve to equilibrate, resulting in rapid warming of the tip, allowing for disengagement of the tip from tissue.

43. A method as recited in claim 21 and further including activating a cutoff valve in the outflow tract of the probe to obstruct outflow and cause the pressures across the Joule-Thomson valve to equilibrate, resulting in rapid warming of the tip, allowing for disengagement of the tip from tissue and disengaging the tip from tissue after it is warmed.

44. A method as recited in claim 32 and further including activating a cutoff valve in the outflow tract of the probe to obstruct outflow and cause the pressures across the Joule- Thomson valve to equilibrate, resulting in rapid warming of the tip, allowing for disengagement of the tip from tissue and disengaging the tip from tissue after it is warmed.

45. A method as recited in claim 33 and further including activating a cutoff valve in the outflow tract of the probe to obstruct outflow and cause the pressures across the Joule-Thomson valve to equilibrate, resulting in rapid warming of the tip, allowing for disengagement of the tip from tissue and disengaging the tip from tissue after it is warmed.

46. A method as recited in claim 34 and further including activating a cutoff valve in the outflow tract of the probe to obstruct outflow and cause the pressures across the Joule-Thomson valve to equilibrate, resulting in rapid warming of the tip, allowing for disengagement of the tip from tissue and disengaging the tip from tissue after it is warmed.

47. A method as recited in claim 35 and further including activating a cutoff valve in the outflow tract of the probe to obstruct outflow and cause the pressures across the Joule-Thomson valve to equilibrate, resulting in rapid warming of the tip, allowing for disengagement of the tip from tissue and disengaging the tip from tissue after it is warmed.

48. A method as recited in claim 36 and further including activating a cutoff valve in the outflow tract of the probe to obstruct outflow and cause the pressures across the Joule-Thomson valve to equilibrate, resulting in rapid warming of the tip, allowing for disengagement of the tip from tissue and disengaging the tip from tissue after it is warmed.

49. A method as recited in claim 37 and further including activating a cutoff valve in the outflow tract of the probe to obstruct outflow and cause the pressures across the Joule-Thomson valve to equilibrate, resulting in rapid warming of the tip, allowing for disengagement of the tip from tissue and disengaging the tip from tissue after it is warmed.

* * * * *